United States Patent
Dorr et al.

(10) Patent No.: US 9,182,079 B2
(45) Date of Patent: Nov. 10, 2015

(54) CLOSING DEVICE, HOUSING PART OF A LUBRICANT CONTAINER, DIAGNOSTIC SYSTEM AND DIAGNOSTIC METHOD FOR MONITORING THE OPERATING STATE OF A LUBRICANT IN THE HOUSING PART

(75) Inventors: Bjoern Dorr, Stuhr (DE); Franz Nuscheler, Munich (DE); Sumit Paul, Munich (DE)

(73) Assignee: Airbus Operations GmbH, Hamburg (DE)

( * ) Notice: Subject to any disclaimer, the term of this patent is extended or adjusted under 35 U.S.C. 154(b) by 886 days.

(21) Appl. No.: 13/263,341

(22) PCT Filed: Apr. 7, 2010

(86) PCT No.: PCT/EP2010/002184
§ 371 (c)(1),
(2), (4) Date: Feb. 1, 2012

(87) PCT Pub. No.: WO2010/115618
PCT Pub. Date: Oct. 14, 2010

(65) Prior Publication Data
US 2012/0123738 A1    May 17, 2012

Related U.S. Application Data

(60) Provisional application No. 61/167,395, filed on Apr. 7, 2009.

(30) Foreign Application Priority Data

Apr. 7, 2009    (DE) .......................... 10 2009 016 642

(51) Int. Cl.
*F16N 29/00* (2006.01)
*F16N 29/04* (2006.01)
(Continued)

(52) U.S. Cl.
CPC ................ *F16N 29/00* (2013.01); *F16N 29/04* (2013.01); *G01N 33/2888* (2013.01); *G07C 3/08* (2013.01);
(Continued)

(58) Field of Classification Search
CPC ....................................................... F16N 29/00
USPC ......................................................... 702/184
See application file for complete search history.

(56) References Cited

U.S. PATENT DOCUMENTS 5,487,760 A * 1/1996 Villafana ....................... 623/2.2
6,392,562 B1 5/2002 Boston et al.
(Continued)

FOREIGN PATENT DOCUMENTS

DE    199 49 994    4/2001
DE    199 49 999    4/2001
(Continued)

OTHER PUBLICATIONS

International Search Report for Application Serial No. WO 2010/115618 A3 dated Oct. 11, 2010.
(Continued)

*Primary Examiner* — Bryan Bui
(74) *Attorney, Agent, or Firm* — Jenkins, Wilson, Taylor & Hunt, P.A.

(57) ABSTRACT

The invention relates to a housing part containing a lubricant reservoir and at least one respective inlet and outlet opening for filling and draining a lubricating fluid into and from the lubricant reservoir. The inlet and outlet openings are sealed by releasable closure devices each comprising a sensor means for determining the operation parameters in a lubricant contained in the lubricant reservoir and for generating and/or storing sensor signals, as well as a transceiver for the transmission of the sensor signals to an external processing unit.

16 Claims, 5 Drawing Sheets

(51) Int. Cl.
*G01N 33/28* (2006.01)
*G07C 3/08* (2006.01)
*G07C 5/00* (2006.01)
*G07C 5/08* (2006.01)
*H04Q 9/00* (2006.01)

(52) U.S. Cl.
CPC .............. *G07C 5/008* (2013.01); *G07C 5/0808* (2013.01); *H04Q 9/00* (2013.01); *F16N 2200/20* (2013.01); *F16N 2250/00* (2013.01); *F16N 2250/04* (2013.01); *F16N 2250/08* (2013.01); *F16N 2260/02* (2013.01); *F16N 2260/06* (2013.01); *F16N 2260/08* (2013.01); *F16N 2260/12* (2013.01); *F16N 2260/18* (2013.01); *F16N 2270/50* (2013.01); *F16N 2270/56* (2013.01); *H04Q 2209/40* (2013.01); *H04Q 2209/84* (2013.01)

(56) References Cited

U.S. PATENT DOCUMENTS

| | | |
|---|---|---|
| 6,459,995 B1 | 10/2002 | Collister |
| 2003/0083794 A1 | 5/2003 | Halm et al. |
| 2006/0105467 A1 | 5/2006 | Niksa et al. |
| 2007/0074563 A1 | 4/2007 | Liu et al. |
| 2008/0077336 A1* | 3/2008 | Fernandes ..................... 702/57 |
| 2008/0289399 A1 | 11/2008 | Cooper et al. |
| 2009/0027227 A1 | 1/2009 | Wilson et al. |

FOREIGN PATENT DOCUMENTS

| | | |
|---|---|---|
| DE | 101 53 151 | 5/2003 |
| DE | 698 10 288 | 11/2003 |
| EP | 1 865 293 | 12/2007 |
| EP | 1 939 602 | 7/2008 |
| WO | WO 01/90539 | 11/2001 |

OTHER PUBLICATIONS

International Preliminary Report on Patentability and Written Opinion for Application Serial No. PCT/EP2010/002184 dated Oct. 18, 2011.

Chinese Office Action for Application No. 201080025273.1 dated Oct. 15, 2014.

Chinese Office Action for Application Serial No. 201080025273.1 dated Dec. 3, 2013.

* cited by examiner

CLOSING DEVICE, HOUSING PART OF A LUBRICANT CONTAINER, DIAGNOSTIC SYSTEM AND DIAGNOSTIC METHOD FOR MONITORING THE OPERATING STATE OF A LUBRICANT IN THE HOUSING PART

RELATED APPLICATIONS

The present application is a national stage entry according to 35 U.S.C. §371 of PCT application No.: PCT/EP2010/002184 filed on 7 Apr. 2010, which claims priority from German Application No.: 10 2009 016 642.4, filed on 7 Apr. 2009, and from U.S. Provisional Application No. 61/167,395, filed on 7 Apr. 2009, the entire disclosures of which are incorporated herein by reference.

TECHNICAL FIELD

The invention relates to a closure device for a lubricant container, a housing part of a lubricant container, a diagnostic system, and a diagnosing method for monitoring the operational condition of a lubricant in the housing part.

The invention relates in particular to a housing part partially or entirely constituting a lubricant container for partially or entirely receiving a power transmission mechanism which includes at least one inlet and/or outlet opening for filling and draining a lubricant into and from the housing part, wherein the inlet and outlet openings are sealed by means of releasable closure devices.

BACKGROUND

Housing parts comprising a lubricant reservoir are used for installation into land, air, water or underwater vehicles and serve there for receiving movable mechanical components such as particularly transmissions or rotary actuators, wherein these movable components are bathed in the lubricating fluid accommodated in the lubricant reservoir of the housing part, whereby they are lubricated and also cooled in a given case.

From DE 101 53 151 A1 a system and a method for the maintenance of actuators of aircraft by using sensors for measuring the humidity content in the actuators are known.

SUMMARY

Embodiments of the invention provide a device and a diagnostic system and a diagnosing method making it possible to efficiently detect or monitor the operational condition of lubricant used in mechanical apparatus such as, e.g., actuators.

The solution in accordance with various embodiments of the invention allows in particular to monitor the effects of extreme fluctuations of the external environmental conditions to which such housing parts on vehicles are exposed in practical use, which may bring about an undesirable inclusion of condensed water in the lubricant reservoir or other undesirable reactions of the lubricant, and which may negatively influence the consistency of the lubricant composition.

By way of example, this set of problems is explained in more detail in the following by making reference to components that are installed in the high lift system of an aircraft: The high lift system of an aircraft is made up of numerous system components that are for the most part, due to their placement, directly exposed to the environmental conditions. During variations of altitude (i.e., climb or descent) the environmental conditions such as external temperature, external air pressure, and atmospheric humidity are subject to change. Hermetic sealing is not possible for most system components and thus also for the rotary actuators in the high lift system, for which reason dynamic seals are frequently employed.

Such seals are, however, not capable of preventing temperature, air pressure and atmospheric humidity from varying all the time within the system components. Depending on climbing rate and sink rate, however, these variations occur more or less at a time delay from the variations of the environmental conditions. This means that during the climb, the air pressure within a system component will always be somewhat higher than the outside air pressure, and during the descent the air pressure within the system components will generally be somewhat lower than the outside air pressure.

An increased pressure consequently acts on the component during the landing approach, so that—especially in (tropical and subtropical) regions of high atmospheric humidity—condensed water forms inside the system component. While the high lift system of an aircraft is being extended, rotary actuators are driven via a transmission shaft system. The actuators contain lubricant of the semifluid type (semifluid low-viscosity greases). If the gears inside the actuator are caused to move during an adjustment of the high lift flaps while condensed water has entered into the actuators, the semifluid mixes with the penetrated water. This process repeats itself with an increasing number of flights, so that the water content in the semifluid increases. From a certain degree of humidity the low temperatures at cruising altitude bring about the risk of ice forming in the actuator, which may in the worst case result in jamming while the flaps are being extended. Should this scenario occur, the high lift system would not be available to the pilot any more during the landing approach.

Previously this problem was generally dealt with by regularly replacing the semifluid while observing certain maintenance intervals. For maintenance, initially the shut-off screws on the housing part are removed, after which the semifluid may drain through the lower outlet. Once semifluid ceases to flow out, the lower shut-off screw together with the sealing washer is mounted again. Then a hose, the second end of which leads into a collecting receptable, is fixed at the upper outlet opening. Following removal of the shut-off screw, the new semifluid may be supplied via the inlet valve with the aid of a grease gun. Following successful filling with the fixed filling quantity, the inlet and outlet openings are closed by means of the corresponding shut-off screws. If the maintenance intervals are not observed, or in the event of an elevated degree of humidity, the semifluid becomes increasingly more viscous, in which case a replacement will only be possible by opening the housing lid. In that case, however, the maintenance effort is so time-consuming that a full replacement of the housing part will frequently be effected for economic reasons. From the maintenance point of view it is a drawback of this known manner of preceeding that the semifluid must be replaced at regular intervals in the above-described manner in order to avoid jamming. As the water content in the semifluid increases at different rates in dependence on the flight route, it would be necessary under an economic viewpoint to separately determine the optimum time for a semifluid exchange for each aircraft. This prediction is extremely difficult, however, for which reason the semifluid is replaced at fixed maintenance intervals.

If maintenance is performed prematurely, with the humidity proportion amounting to only a few percent, the airline company might have saved the costs for the maintenance. If excessively long maintenance intervals are selected, the airline company risks damage to partial components or even jamming in the actuator, while an elevated degree of humidity may moreover cause the semifluid to become so viscous that it is not possible any more to replace the semifluid without a time-consuming and thus costly operation of opening the rotary actuator—mostly ending up in the component being replaced.

The solution in accordance with the invention allows to avoid or clearly limit the maintenance expenditure described in the foregoing. Aside from the use of the solution in accordance with the invention as described for a flap rotary actuator for the adjustment of a flap (landing flap) on the wing of an aircraft for monitoring the inclusion of condensed water in this flap rotary actuator, the solution in accordance with the invention may also be provided similarly on any kind of housing parts having movable mechanical components in a lubricant reservoir in any land, air, water or underwater vehicles (e.g., automotive vehicles, aircraft, helicopters, ships, submarines, etc.). The use of the solution in accordance with the invention may particularly be provided where undesirable variations of the composition and properties of the lubricant may occur during use of such a vehicle owing to external environmental influences, so that the lubricant composition must be monitored regularly and the lubricant must in a given case be replaced in due time. The invention may thus generally be provided for housing parts intended for installation in a vehicle and having movable components mounted therein inside a lubricant reservoir such as, e.g., transmissions or rotary actuators. What is proposed is a structure wherein a regular diagnosis of the consistency of the lubricant being exposed to external environmental influences may be carried out in the most simple way possible, and that, when such diagnosis yields the result that a replacement of the lubricant has to be effected, the replacement operation may be carried out in the most simple way possible. In addition a diagnostic system and a diagnosing method are provided which allow the most simple monitoring possible of the operational condition of the lubricant in the lubricant reservoir inside a housing part including movable mechanical components.

What is provided in accordance with the invention is a closure device for sealing an opening of a housing part from a lubricant, which comprises an internal space, the internal space of the closure device comprising:

at least one sensor device comprising a sensor for generating sensor signals corresponding to the operational condition of the lubricant, at least one transceiver for receiving the sensor signals from the sensor device and for signal transmission of the sensor signals to an external reception unit, a power supply device for supplying electric power to the sensor device and to the transceiver, wherein the surface of one end portion is realized as a sensor surface for the detection of the sensor values.

Due to the provision of a sensor device in a closure device, the sensor device comprising the closure device may readily be replaced while a separate and complex integration and control activity is not required for inserting the closure device in the location intended for it, e.g., an opening of a housing part. Moreover the logistic effort for replacement parts for the sensor device is simple as it is readily possible to replace the closure devices.

The closure device of the invention may be realized as a screw and for insertion in a threaded reception of an inlet opening or outlet opening, or as a bolt having a securing element for closing, e.g., a respective inlet opening or an outlet opening by means of the bolt.

The transceiver may in particular be adapted for establishing a wireless transmission connection for transmitting the sensor signals to an external reception unit and may be coupled to an antenna which is disposed on a surface of a second end portion situated opposite from the first end portion.

It may further be provided that the sensor device comprises a humidity sensor for detecting the water content of the lubricant and/or a temperature sensor for detecting the temperature of the lubricant and/or a pressure sensor for detecting the pressure of the lubricant. In particular a combination of the measurements of water content or humidity content and of the temperature of the lubricant may be performed, whereby the measurement of the water content may be carried out more accurately. In this practical example, the measurement function integrated in the sensor device determines the water content as a function of the equally measured temperature of the lubricant.

According to a further practical example, the sensor device may include a measurement function wherein at least one temporal specification for the performance of a measurement and a function of performing the measurement are set up, which measurement function activates the sensor when the temporal specification is satisfied and detects sensor signals for the determination of sensor values. The temporal specification may be realized through a timer of the sensor device which is coupled to the measurement function such that the measurement function carries out a measurement of the operational condition of the lubricant in response to an activation signal of the timer. In this case the measurement value for the operational condition of the lubricant is stored in a memory device from where the measurement value may be read out in response to a query, e.g. by an external maintenance device, and transmitted to the maintenance device. This practical example presents the advantage that the closure device comprising the sensor device may be realized in a very simple manner. The sensor functions for the measurement may moreover be operative independently of external devices such as, e.g., the maintenance device. As a result, the measurement function for performing the measurement particularly does not need to have an interface with an external device.

According to one practical example, the transceiver may alternatively or additionally comprise a driving device which is functionally communicated with the sensor device and activates the measurement function of the sensor device by means of an activation signal in response to reception of a measurement command for performing a measurement, so that the sensor device detects at least one sensor signal for the determination of sensor values and transmits it to the transceiver.

The sensor device may comprise, or be made up of, a planar capacitor which is constituted by two capacitor parts facing each other. Alternatively, the sensor device may comprise a plate capacitor having two capacitor plates. In this case the sensor surface of the first end portion intended for entering into contact with the lubricant may in particular be realized partly as a groove, with two mutually facing surfaces of the side walls of the groove each forming an outer side of a respective one of the capacitor plates. The groove may in particular be an annular groove. In these embodiments it is provided in particular that in order to measure the operational condition of the lubricant, the sensor surface intended for entering into contact with the lubricant is arranged on the closure device in such a way as to face the inside of the housing part when the closure device is in the closing state.

According to a further aspect of the invention, a housing part of a lubricant container is provided which comprises a sensor device according to the invention that is adapted for generating sensor signals corresponding to the operational condition of the lubricant contained in the housing part. In particular it may be provided that the housing part comprises at least one opening and a closure device adapted to be inserted therein and comprising a sensor device in accordance with the invention. The closure device may in particular be realized in accordance with one of the presently described practical examples. The housing part and the closure device may furthermore be configured such that in the state of the closure device in which it closes the housing part, a surface of a first end portion of the closure device faces the interior of the housing part so as to be in contact with the lubricant, wherein the surface is realized as a sensor surface for the detection of the sensor values.

According to a further practical example of the invention it is provided that the housing part has at least one outlet opening or inlet opening for draining the lubricant from the housing or lubricant container in the composite state, the part of which is the housing part, and that the at least one outlet opening or inlet opening, respectively, is sealed by the releasable closure device. The closure device may be realized as a screw, and the respective opening of the housing part may have a threaded reception for receiving the screw. The closure device may moreover be realized as a bolt having a securing element for closing the respective inlet and outlet openings by the bolt. Due to the provision or insertion of a closure device of the invention in an outlet opening or inlet opening of the housing part of a lubricant container, an opening which at any rate is already provided, in a given case for a different purpose, may additionally be provided for the integration of a sensor device of the invention. In this way a separate mechanical integrating effort is not required for integrating the sensor device provided in accordance with the invention in the housing part or in the lubricant container, respectively.

The housing part of the invention constituting a lubricant container may in particular be a housing part of a power transmission mechanism. In particular, the transmission mechanism may be a transmission, or gearing. The transmission may moreover be the transmission of an rotary actuator.

According to a further aspect of the invention a diagnostic system is provided, comprising: a housing part comprising a sensor device in accordance with one of the practical examples presently described and a transceiver associated thereto, and a maintenance device comprising a transceiver for receiving sensor signals from the transceiver associated to the sensor device, wherein the maintenance device includes a processing function for determining, on the basis of the sensor signal, a value for the operational condition of a lubricant present in the housing part. According to one practical example, the maintenance device is releasably or fixedly installed in the vehicle in which the lubricant container comprising the housing part is also integrated. Alternatively or additionally it may be provided that the maintenance device is a mobile maintenance device which may in particular be realized as a hand-held apparatus.

In the diagnostic system it may be provided that the sensor device includes a measurement function wherein at least one temporal specification for the performance of a measurement and a function of performing the measurement are set up, which measurement function activates the sensor when the temporal specification is satisfied and detects sensor signals for the determination of sensor values, that the maintenance device comprises an input device functionally communicated with the transceiver for retrieving a sensor value, which input device drives the transceiver of the closure device in response to an actuation of the input device, activates it for the transmission of a signal corresponding to the detected sensor signal, and receives this signal. In this practical example it may in particular be provided that measurement signals are generated with the aid of the timer through the measurement function and are stored in the memory device. In response to the activation signal by the maintenance device, the measurement signal or a sensor value determined from the latter is transmitted via the transceiver to the maintenance device where it may be displayed.

It may furthermore may be provided that the sensor device is configured such that in response to receiving a control command from the transceiver associated to the sensor device, it detects a sensor signal corresponding to an operational condition of the lubricant and transmits it to the maintenance device.

According to one practical example of the diagnostic system of the invention it is provided that the sensor device includes: a processing function for determining a value for the operational condition of a lubricant present in the housing part on the basis of the detected sensor signal, and a diagnosis function functionally communicated with the processing function for determining maintenance information from the respective determined value for the operational condition of a lubricant present in the housing part. In this way the maintenance function does not need to include any sensor-specific evaluation or diagnosis function. If the sensor is replaced, the maintenance device does not need to be adapted as in this case it does not include a specific evaluation and diagnosis function. Moreover, the evaluation or diagnosis function in the sensor device may be adapted to each single sensor, for instance in order to calibrate or match the sensor evaluation or the specific sensor. Alternatively, the diagnosis function may be integrated in the maintenance device.

The maintenance device may comprise a display device for displaying the sensor quantities and/or determined maintenance information. Moreover the maintenance device may be a hand-held maintenance apparatus in which the processing function and the display device are structural.

According to a further aspect of the invention, a diagnostic system having a maintenance device in accordance with one of the embodiments of the invention is provided, wherein the maintenance device includes a comparison function functionally communicated with a sensor device for supplying sensor signals realized in accordance with the invention, which is realized in such a way that the comparison function compares the respective detected measurement signal to two limit values and identifies, based on this comparison, whether the respective detected signal value is situated in a first range below a first limit value or in a second range between the first limit value and a second limit value greater than the first limit value, or in a third range above the second limit value. In this case the maintenance device includes a display function which carries out, based on the identification of a range for the respective detected signal value, marking of one of three fields each associated to one of the ranges in a display format of the display device. The comparison function may also be integrated in the sensor device, so that the sensor device determines information concerning the allocation of the signal value determined therein to the first, second or third range, which information is transmitted to the display device and displayed by the latter. By way of example, the third range may designate a critical range, the affirmation of which is to indicate the performance of replacing the component in which the sensor device is integrated. Here the first range may designate an admissible range, the affirmation of which is to indicate that the component is in an admissible operational condition and no maintenance measures are required. The second range may designate an admissible range, the affirmation of which is to indicate an operational condition of the component which, although admissible, forebodes a maintenance measure or requires a specific maintenance measure.

Allocation to the first and/or second range and displaying the presence of the first and/or second range may also be omitted. Accordingly, the maintenance device of the invention may include a comparison function which is functionally communicated with the sensor device for supplying sensor signals and realized such that the comparison function compares the respective detected measurement signal to at least one limit value and identifies, based on this comparison, whether the respective detected signal value is situated in a first range below this limit value or in a second range above this limit value, and such that the maintenance device includes a display function which performs, on the basis of the identification of a range for the respective detected signal value, marking of at least one field or one of two fields each associated to one of the ranges in a display format of the display device. If only one range is provided in the display device and the associated functionality, this range may in particular indicate a previously mentioned critical range. If two ranges are provided in the display device and the associated functionality, one of these ranges may in particular indicate a previously mentioned critical range, and the other range an admissible range.

Moreover it may be provided that the maintenance device comprises a function module whereby a value for an operational condition of a lubricant present in the housing part may be selected, whereby a maintenance information necessary for a maintenance task may be transmitted to a display means and displayed by means of the display means.

According to a further practical example of the diagnostic system of the invention it is provided that at least two sensor devices are integrated in the housing part, that the maintenance device includes a comparison function functionally communicated with the transceiver of the maintenance device, and a comparison function value which is used as a value for the operational condition of a lubricant present in the housing part is formed on the basis of the sensor signals from two different sensor devices. It may moreover be provided that the comparison function is realized in such a way that it uses the respective greatest signal value of the different sensor devices of a lubricant container as a determined signal value to be displayed. This practical example presents the advantage that the security of determination and display of the lubricant condition is enhanced. In this case not only local differences of the operational condition of the lubricant but also errors at the sensor device or at a component part of the closure device may be compensated.

The transceiver of the maintenance device and the transceiver associated to the closure device and in particular belonging to the closure device may be functionally communicated with each other in a cordless manner or via a cable connection.

According to a further aspect of the invention, a diagnosing method for assisting the maintenance of a land, air, water or underwater vehicle is provided, including the steps of:
   generating a sensor signal for detecting an operational condition of a lubricant contained in the housing part with the aid of a sensor device integrated in a closure device of the housing part, and transmitting the sensor signal corresponding to the operational condition to the maintenance device,
   based on the sensor signal transmitted to the maintenance device, determining in the maintenance device a value for the operational condition of a lubricant present in the housing part on the basis of the sensor signal,
   as the result of an actuation of a maintenance device, transmission of a command signal to a transceiver integrated in a housing part of a power transmission mechanism to be monitored, and reception of a sensor signal corresponding to the operational condition of the lubricant by the maintenance device and displaying of the operational condition of the lubricant by means of the maintenance device.

Here it may be provided that the sensor device itself, and in particular in response to activation by the timer, detects a sensor signal corresponding to the operational condition of the lubricant, determines from this a sensor value corresponding to the operational condition of the lubricant, stores the sensor value in a memory, and transmits the sensor value to the maintenance device in response to a request command received from the maintenance device.

Alternatively or additionally it may be provided that the maintenance device sends to the sensor device a request command for transmission of a sensor value corresponding to the operational condition of the lubricant, determination of the sensor value by the sensor device, and transmission thereof to the maintenance device.

According to one practical example of the diagnosing method it may be be provided that a maintenance function is integrated in the maintenance device which determines maintenance information from the value for the operational condition of a lubricant present in the housing part. It may moreover be provided that the maintenance device displays the determined maintenance information by means of a display device.

In particular it may be provided in the diagnosing method that in the process of determining the value for the operational condition of a lubricant present in the housing part based on a sensor signal, a value for the water content in the lubricant bath is determined on the basis of a signal value detected by the sensor device.

In accordance with the invention it may moreover be provided that at least two sensor means are employed in one examination location, the sensor signals of which are transmitted to the processing unit to be compared there, wherein as a result of the comparison a comparison function value is formed which is underlaid the further processing. It may moreover be provided that the central processing unit compares the signals received from a sensor assembly group to predetermined limit values for these signals and visualizes on a display whether the received signal is situated within predetermined limit values for the signal. The diagnosing method may be executed in such a way that when a received signal is situated outside the range of the predetermined limit values, the processing unit outputs a warning signal, in particular an acoustic or visual warning signal. If the diagnosing method or the diagnostic system is configured such that the central processing unit receives signals from several sensor assembly groups, it may be provided that the relative position of the sensor assembly groups among each other and/or relative to the vehicle body of a land, air, water or underwater vehicle in which the sensor assembly groups are installed is displayed on the display device.

In the diagnosing method it may moreover be provided in particular that the maintenance device forms, based on the sensor signals of two different sensor devices each integrated in the housing part, a comparison function value which is used as a value for the operational condition of a lubricant present in the housing part, wherein in particular the respective largest one of the measurement values determined within a measurement period is used as a comparison function value.

In the diagnosing method the transmission of a command signal from the maintenance device to the transceiver integrated in the housing part and the transmission of the sensor signal from the transceiver to the maintenance device may take place in a cordless manner.

According to a further practical example it is provided that a satellite position sensor is integrated in the sensor device, or one respective satellite position sensor in each sensor device if several sensor devices or closure devices are used in one lubricant container, whereby the position of the closure device is determined. Here it may moreover be provided that this position is stored in the sensor device and in particular in a memory device thereof, and is transmitted to the maintenance device upon a query, optionally together with a respective sensor value.

In the diagnosing method of the invention it may be provided that sensor signals are generated and/or stored in at least one sensor device on high-maintenance partial systems or components of the vehicle in an examination location, the sensor signals being transmitted to the maintenance device which determines an operational condition on the basis of the sensor signals of different partial systems.

According to a further aspect of the invention, a land, air, water or underwater vehicle is provided in which a housing part of the invention and/or a diagnostic system of the invention is installed.

BRIEF DESCRIPTION OF THE DRAWINGS

The advantages and features of the present invention also become evident from the following practical examples in conjunction with the drawings, wherein.

DESCRIPTION

The closure device of the invention, the housing part of the invention, the diagnostic system of the invention, and the diagnosing method of the invention shall be explained in the following, in particular also on the example of an aircraft, and then in particular on the set of problems involved in determining the concentration of water inclusions in a lubricant reservoir.

According to one aspect of the invention, a closure device 20 for sealing an opening of a housing part 10 from a lubricant is provided which is realized as a screw or bolt and has integrated therein (FIG. 1): a sensor device for generating sensor signals corresponding to the operational condition of the lubricant, as well as a transceiver for the signal transmission of the sensor signals to an external reception unit, with a surface of the closure device 20 being realized as a sensor surface for the detection of the sensor values.

According to a further aspect of the invention, a housing part of a lubricant container is provided with such a closure device for sealing or for closing an inlet or outlet opening of the lubricant container. The housing part may generally be part of a lubricant container or entirely constitute the latter. The lubricant container comprising the housing part 10 of the invention may generally be intended for serving a reservoir or storage function. Alternatively or additionally, the lubricant container may be implemented with the housing part 10 of the invention for receiving a power transmission mechanism 11 and at the same time as a lubricant container for receiving the lubricant required for lubrication of the power transmission mechanism 11.

Figure 1:
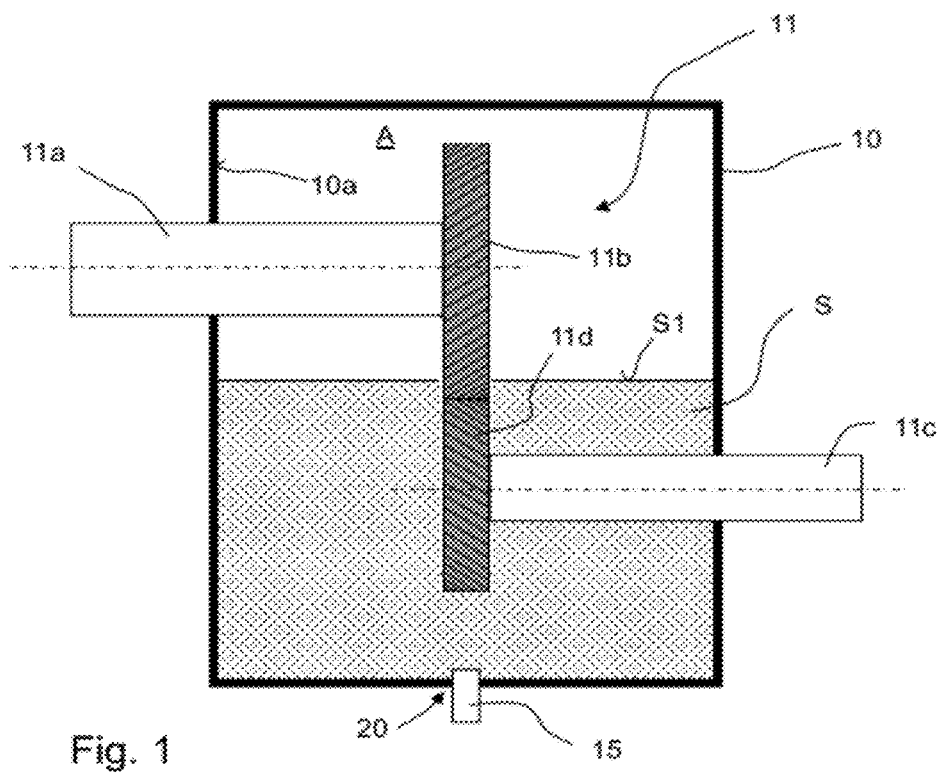
FIG. 1 is a schematic sectional view of a power transmission mechanism having the form of a transmission, or gearing, which is accommodated in a housing part having the form of a lubricant container, wherein the housing part includes, in accordance with the invention, an outlet opening closed by a closure member.

In FIG. 1 a housing part 10 of the invention having a power transmission mechanism 11 arranged therein is represented schematically. This sectional representation shows the power transmission mechanism 11 accommodated in the housing part to have the form of a transmission comprising an input shaft 11a, a transmission wheel 11b arranged thereon and having the form of a gearwheel, an output shaft 11c, and a second transmission wheel or driven gear 11b arranged thereon and having the form of a gearwheel. Inside the housing part 10, which is formed integrally in the representation of FIG. 1, a lubricant S or a lubricating fluid for lubrication of the transmission mechanism 11 is present which is particularly in the liquid state in operational use.

In accordance with the invention, the housing part 10 has at least one inlet opening and/or at least one outlet opening for filling the lubricant S into the lubricant container or for draining the lubricant therefrom, each of which is sealed by a releasable closure device 20. The housing part 10 represented in FIG. 1 has an outlet opening 15 for draining the lubricant S in which the closure device 20 is inserted, so that after removal of the closure device 20 the outlet opening 15 is open and lubricant may escape through it from the housing part 10.

Here it may be provided that for the intended operation of the housing, or of the housing part, the lubricant does not entirely fill the housing or the housing part 10, resulting in the formation of a surface level S1 of the lubricant S in the housing or housing part 10. In this case, an opening of the housing part 20 of the invention in which a closure device of the invention comprising a sensor device is inserted is situated in a range below the surface level S1 of the lubricant S of the housing comprising the housing part 10 of the invention when the housing or the housing part 10 is assembled or installed in its intended location, so that during operation of the housing or of the housing part 10, the opening or the sensor device is situated in or at a lubricant-filled area in the normal condition. Hereby it is ensured that the operational condition of the lubricant may be detected in the normal condition.

In the application in which the housing is filled only partly with lubricant for the operational condition of the housing comprising the housing part 10 of the invention, the opening having a closure device of the invention inserted therein may in particular be a lubricant outlet opening that is situated, at an intended orientation of the housing, below the surface level S1 of the lubricant S present in the housing for the operation.

In a specialized exemplary application of the invention in which the housing part is a part of a housing or the housing for a power transmission mechanism 11 and in particular a rotary actuator for adjusting an aerodynamic flap of an aircraft (FIG. 2), it may in particular be provided that the housing comprising the housing part of the invention is filled with lubricant to no more than between 40% and 80% of the housing capacity. The installation of the housing comprising the housing part of the invention and the position of the opening on the housing are provided such that the opening with the closure device of the invention is situated below the surface level S1 of the lubricant S present in the housing for the operation.

Figure 2:
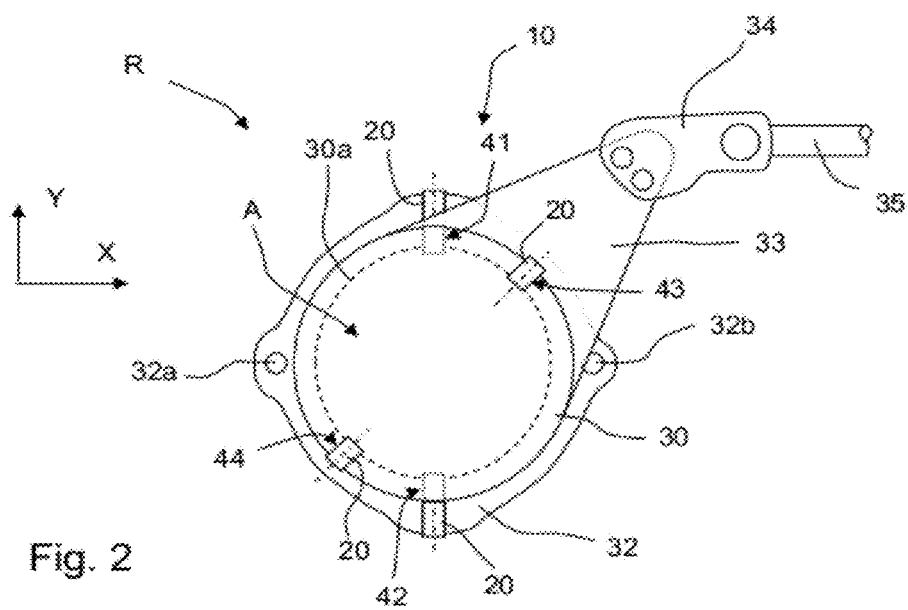
FIG. 2 is a schematic top view of a practical example of a rotary actuator comprising a base plate and a housing part having the form of a lubricant container, wherein a power transmission mechanism implemented as a transmission is received.

The practical example of a housing 10 of the invention represented in FIG. 1 is intended for receiving a rotary actuator R as a power transmission mechanism 11 and is made up of a rotatable housing part 30 and a second housing part realized as a base body 32 or flange body, wherein the housing part 30 is rotatably mounted on the base body 32. The base body 32 is intended for fastening to a structural component and has two flange bores 32a, 32b for this purpose. The rotatable housing part 30 forms on its inner side 30a an internal space A that is partly delimited by the inner side of the base body 32 facing this internal space. In FIG. 2 the inner wall 30a of the rotatable housing part 30 is represented as a dashed line. In the internal space A a transmission mechanism 11 (not represented) is installed, whereby an input power transmitted by an input shaft to the transmission mechanism 11 is transmitted by the transmission mechanism 11 to an output shaft (not represented). The transmission mechanism 11 may have the form of a transmission, and in particular a gearwheel transmission. The output shaft is coupled to an adjusting lever 33 that is coupled via a coupling device 34 to a transmission rod.

The represented rotary actuator R may in particular be used for adjusting an aerodynamic flap of an aircraft. The aerodynamic flap may in particular be a trailing edge flap of a main wing of the aircraft. In this application the base body 32 is fastened to a structural component of the main wing, and the transmission rod is coupled to the aerodynamic flap or the trailing edge flap, respectively.

The housing part 10 of the invention may in particular be a housing part that is movable or rotatable relative to another housing part, with a dynamic seal being arranged between the housing parts. In the present context a "dynamic seal" is understood to be a seal which is arranged between parts that are movable relative to each other and, although sealing the internal space formed by those parts with respect to a lubricating fluid present in this internal space, nevertheless does not completely seal the internal space with respect to air. The housing part 10 of the invention may also be a housing part 10 having a recess through which protrudes a rotating part such as, e.g., an input shaft or generally a part that is movable relative to the housing part, wherein a dynamic seal is arranged between the part moving relative to the housing part and the housing part 10. In this case the housing part also comprises a reception for mounting a dynamic seal.

The housing part of the invention may, but need not exclusively, have the form of a lubricant container and need not exclusively be provided for the purpose of lubricant reception. As may be seen in FIG. 1, the housing part 10 may also have the function of a cover as well as, for instance, also the function of an adjusting element which is realized in the practical example according to FIG. 1 as an adjusting lever 33. The housing part 10, however, is part of a housing or the housing in which lubricant is present for the intended operation.

In the case of the represented rotary actuator R for adjusting an aerodynamic flap of an aircraft (FIG. 2) it is in particular provided that the housing comprising the housing part of the invention is filled with lubricant only to a maximum of 80% of the housing capacity. The orientation of the base body 32 represented in FIG. 2 is the orientation in which it is installed in a structural component of an aircraft or fastened thereto. In FIG. 2 an XY-coordinate system is specified in which the Y-direction indicates the direction of gravity. The housing part 30 is shown in a position in which the transmission element 35 holds the flap coupled to it in an extended state. The housing part 30 is thus rotated counter-clockwise when seen in the viewing direction of a person viewing FIG. 2 when the rotary actuator R takes the transmission element 35 to a retracted position.

The practical example of the rotary actuator R represented in FIG. 2 has in the base body 32 an inlet opening 41 for introducing lubricant and an outlet opening 42 for draining the lubricant. The housing part 30 of the rotary actuator R according to FIG. 2 moreover also has an inlet opening 43 for introducing lubricant and an outlet opening 44 for draining the lubricant. According to an alternative practical example it is also possible that only one inlet opening and only one outlet opening are provided on the rotary actuator R according to FIG. 2, wherein in this case the inlet opening and the outlet opening may each be disposed on the base body 32 and/or on the rotatable housing part 30.

As the installation of the housing comprising the housing part of the invention and the position of the opening having a closure device according to the invention is provided on the housing such that the opening having the closure device of the invention is situated below the surface level S1 of the lubricant S present in the housing for the operation, in the represented practical example the outlet openings 42, 44 are each provided with a closure device according to the invention. Alternatively it is also possible that only one of the outlet openings, i.e. the outlet opening on the base body 32 or the outlet opening on the rotatable housing part 30, is provided with the closure device of the invention. In each of the further openings a closure device without a sensor device may be inserted for closing it.

Figure 3:
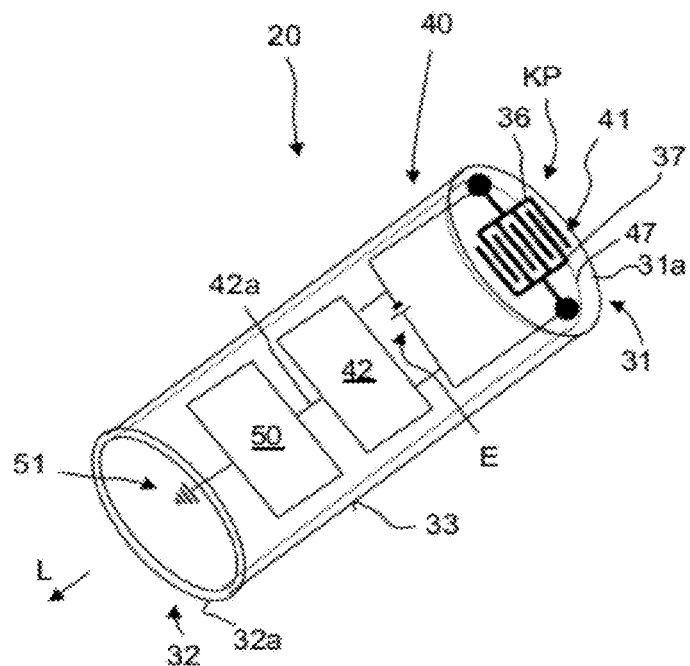
FIG. 3 is a schematic representation of a practical example of a closure member provided in accordance with the invention and having an end portion realized as a capacitor, in which a sensor device and a transceiver as well as a power supply for the capacitor are functionally integrated, and wherein the capacitor is implemented as a planar capacitor.
Figure 5:
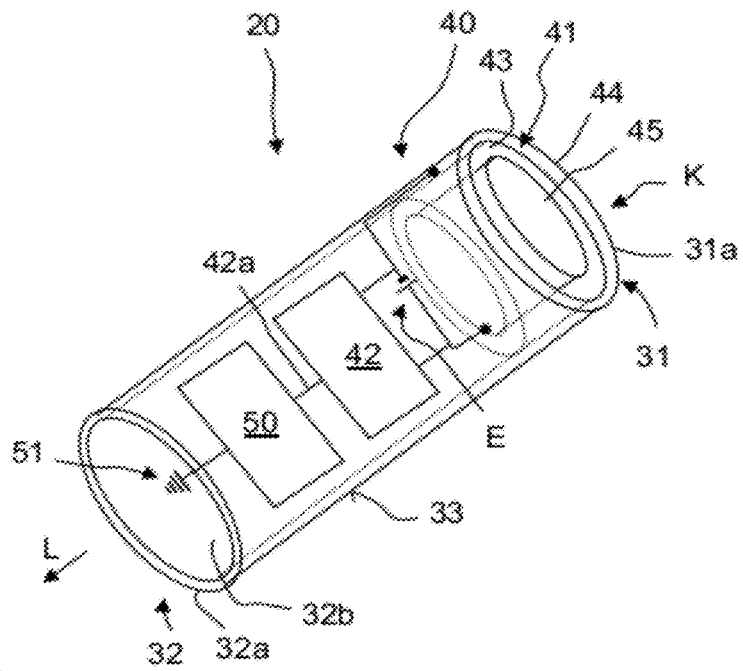
FIG. 5 is a schematic representation of a further practical example of a closure member provided in accordance with the invention and having an end portion implemented as a capacitor, into which a sensor device and a transceiver as well as a power supply for the capacitor are functionally integrated, wherein the capacitor is realized with ring-shaped capacitor surfaces.
Figure 6:
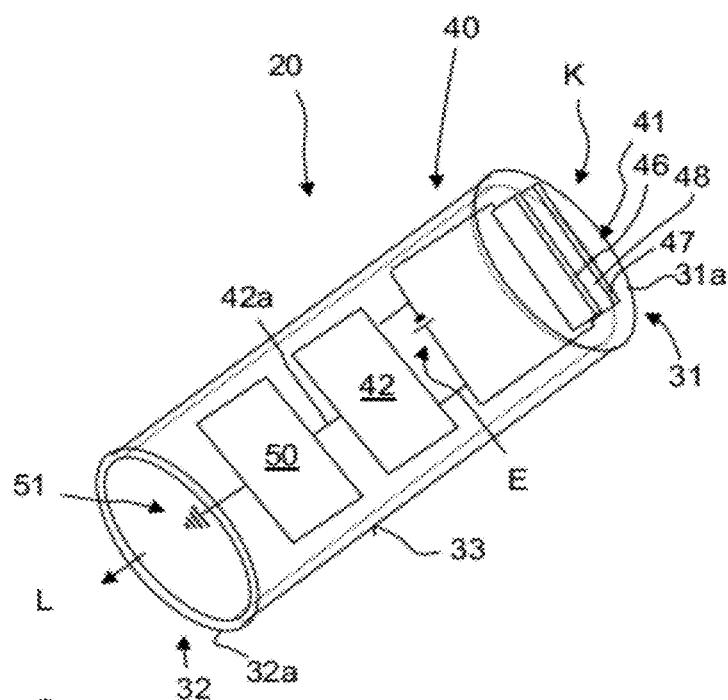
FIG. 6 is a schematic representation of a further practical example of a closure member provided in accordance with the invention and having an end portion implemented as a capacitor, into which a sensor device and a transceiver as well as a power supply for the capacitor are functionally integrated, wherein the capacitor is realized as a plate capacitor.

FIGS. 3, 5 and 6 represent two embodiments of the closure device of the invention 30 which generally has a first end portion 31 with a first end surface 31a, a second end portion 32 situated opposite therefrom with a second end surface 32a, and a longitudinal side 33 or outer side extending along the longitudinal direction L. In the closure device 20 there are disposed a power supply device E, a sensor device 40 comprising a sensor 41 and a signal processing device 42, and a transceiver 50 functionally communicated with the signal processing device 42 via a connecting line 42a, or a receiver/transmitter comprising a signal transmission device 51 for transmitting output signals generated by the signal processing device 42 to an external reception device and for receiving driving signals from an external reception device.

According to one practical example, the closure device of the invention 20 has the form of a screw and is configured for being inserted in a threaded reception of an opening, i.e., the inlet opening or the outlet opening. To this end, the longitudinal side 33 is realized with an external thread (not shown) and the respective opening with an internal thread (not shown). Alternatively, the closure device according to the invention may have the form of a bolt comprising a securing element for closing the respective opening, i.e., the inlet or outlet opening by the bolt. The closure device of the invention may moreover be designed as some other releasable closure member.

In accordance with the invention, the sensor 41 of the sensor device 40 generally is a sensor adapted to detect operation parameters of the lubricant such as, e.g., the temperature, the pressure and/or the water content in the lubricant, or humidity of the lubricant, through immersion in the lubricant bath at the closure device 20 inserted in the housing part, due to the circumstance that the first end surface 31a of the first end portion 31 is in contact with the lubricant. The first end surface 31a here forms a component part of the sensor 41 and is adapted for detecting the respective operation parameter.

In order to detect the water content in the lubricant, the sensor may be realized as a capacitor K. In this case the end surface 31a may in particular be formed of two capacitor plates or generally of capacitor parts in order to detect the effect of the dielectric properties of the lubricant along the impedance/capacitance measurement principle. The end surface 31a may also have two capacitor parts. Alternatively, the first end surface 31a or the sensor device 40, respectively, may consist of a planar capacitor KP having two capacitor surfaces 36, 37 engaging each other in surface contact or in a fork-type configuration in order to maximize the size of the mutually facing boundary lines or boundary surfaces (FIG. 3). The outwardly directed planar capacitor partial surfaces of the planar capacitor electrodes or planar-capacitor partial plates 36, 37 extend in the end surface 31a. Between the planar capacitor electrodes 36, 37 a groove may be provided or an insulation material may be provided. In another practical example, the capacitor parts may be two antennae projecting from the first end surface 31a (not represented in the figures).

Figure 4:
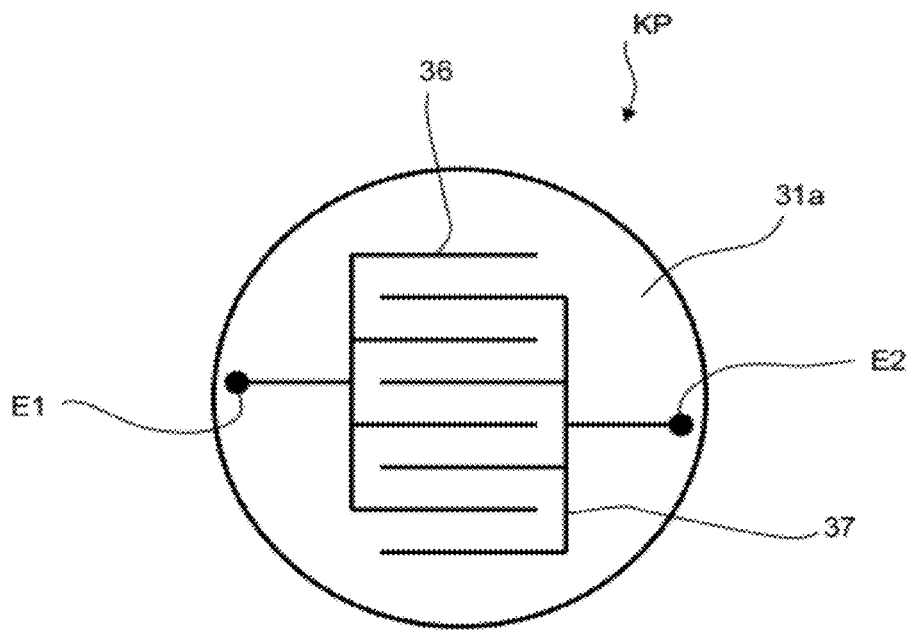
FIG. 4 is a schematic representation of the end portion implemented as a capacitor and comprising a planar capacitor of the capacitor represented in FIG. 3.
Figures 7A, 7B:
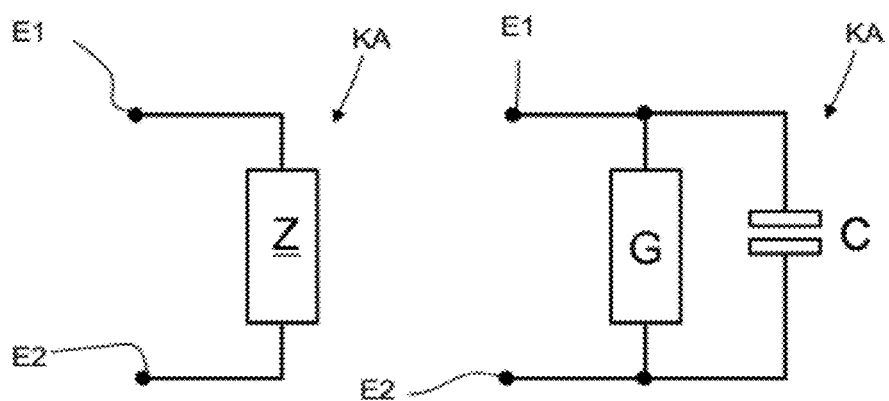
FIG. 7a is an equivalent circuit diagram for electrical driving of a plate capacitor represented in FIGS. 3, 5 and 6.
FIG. 7b is another equivalent circuit diagram for electrical driving of a plate capacitor represented in FIGS. 3, 5 and 6.

The power supply device E is used to apply AC voltage to the capacitor parts or to the capacitor plates of the respective capacitor provided or of the capacitor assembly KA. In order to represent the connection of the power supply device E to the respective capacitor parts, in the represented example to the planar capacitor electrodes 36, 37, contact locations E1 and E2 are drawn schematically for clarity in FIG. 4; these need, however, not be provided in a realization of the represented devices. In a measurement function an impedance is determined from the applied AC voltage, as is represented schematically in FIG. 7a showing an electric equivalent circuit diagram. The impedance of a capacitor is determined by its geometry and the electric properties of the dielectric placed between the capacitor plates. In a general way, the impedance may be considered to be a complex resistance. Alternatively or additionally it may be provided that a capacitor provided in accordance with the invention and having an AC voltage applied thereto is used to measure an amplitude and/or a phase shift and/or an attenuation each presenting the measured AC voltage relative to the applied AC voltage in order to determine from this, e.g. in the sensor device or by means of the measurement function, a relative permittivity epsilon-r ($\in$r). In FIG. 7b an equivalent circuit diagram of a technical realization of an embodiment of a capacitor assembly KA provided in accordance with the invention and including a capacitor C and a resistor G connected in parallel with the latter is represented, which may be used to determine the mentioned measurement signals or measurement quantities. In the capacitor C the stored electric power is described, and in the parallel conductance G the conductivity.

According to a further practical example of the the invention, the capacitor K may be realized by forming a peripheral groove 43 in the end surface 31a, so that the end portion 31 is formed by a peripheral capacitor ring 44 at the outer margin of the first end surface 31a, and a capacitor die 45 formed within the latter (FIG. 5). The mutually facing surfaces of the capacitor ring 44 and of the capacitor die 45, i.e. the inner surface of the capacitor ring 44 and the outer surface of the capacitor die 45 form the mutually facing capacitor surfaces between which the lubricant is present whose water content or degree of humidity is to be measured with the aid of the capacitor K. Alternatively, the end portion 31 or the sensor 41, respectively, may also have the form of a plate capacitor having two capacitor plates 46, 47 extending, e.g., in parallel and from the first end surface 31a, and an interstice 48 located between these in accordance with FIG. 6.

According to a practical example of the invention, the sensor 41 is realized such as to be capable of detecting a range from 0% to 40% of relative humidity. The advantage of the sensors provided in accordance with the invention and in particular of the utilization of capacitors for determining the humidity is that it is possible to achieve such measurement ranges and required measurement accuracies.

In particular as a result of realizing the sensor in the form of a capacitor sensor having structurally realized capacitor plates, the very lubricating agent is used as a dielectric. The measurement signal is essentially determined by the relative permittivity. Lubricants have a relative permittivity $\in$r (epsilon-r) of approx. 3-5. Water on the other hand has, due to the innermolecular hydrogen bond, a relative permittivity $\in$r (epsilon-r) of approx. 80. It is therefore very well possible to discriminate between water and lubricating agent and to very easily detect and ascertain the water content in lubricating agents.

The sensor device 40 may in particular comprise a signal processing device 42 functionally communicated with the sensor 41, which detects the electric signals of the sensor. The signal processing device 42 may also include a comparison function which compares the detected sensor signals corresponding, depending on the sensor, to a humidity content, a pressure or a temperature, to a limit value or to several limit values, and which generates an output signal indicating that the sensor signal is below a limit value, exceeds a limit value, or is situated between two limit values, and displays this.

The sensor device 40 and in particular the signal processing device 42 may be functionally communicated with the transceiver 50 for receiving the sensor signals and/or the output signals from the sensor device and for the signal transmission of the sensor signals to an external reception unit via a connecting line 42a. To this end, the transceiver 50 is connected to a signal transmission device 51. According to the practical examples represented in FIGS. 3, 5 and 6, the signal transmission device 51 has the form of an antenna for the wireless transmission of signals and information to an external reception unit, to which in turn a signal processing device for further processing and in particular for evaluating the necessity of maintenance measures is coupled. Alternatively, the signal transmission device 51 may be realized with a wire or cable connection to the external reception unit.

The external reception unit is a unit externally of the closure device, and in particular a unit externally of the housing comprising the housing part 20 of the invention. Here the external reception unit may be part of a hand-held maintenance apparatus H.

This cordless implementation of the signal connection between the transceiver 50 and an external processing device or external maintenance device results in a particularly simple and compact construction, for additional cabling is saved, and in case a sensor or a transceiver should malfunction, it would be sufficient to simply replace the closure device 20 having the deficient sensor/transceiver with a closure device 20 having a functional sensor/transceiver without having to release or fasten further plug connections.

The transceiver 50 may be disposed in a recess of a second end portion 32 of the closure device 20 having the form of a head end and disposed opposite from the first end portion 31, wherein the second end portion 32 of the closure device has an outer side 32a which forms an outer side of the housing part 10, 30 when the closure device is in the state closing the housing part 10, 30, and wherein an inner area of the outer side of the second end portion of the closure device has an opening 32b of the recess for wireless transmission of the sensor signal to an external reception unit. Here a resin layer having transmissibility for the wireless transmission waves may be inserted in the opening 32b. The outer side of the second end portion 32 of the closure device having the opening may also be covered entirely or partially by a resin layer.

Figure 8A:
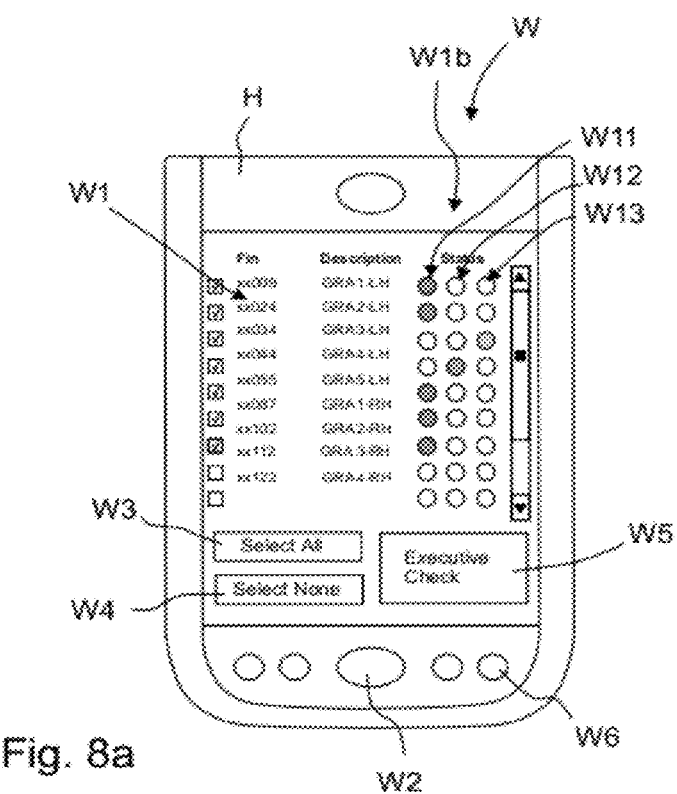
FIG. 8a shows a practical example of a maintenance device usable for the diagnostic system of the invention or the diagnosing method of the invention, which is realized as a hand-held apparatus, with a practical example of a diagnostic display.
Figure 8B:
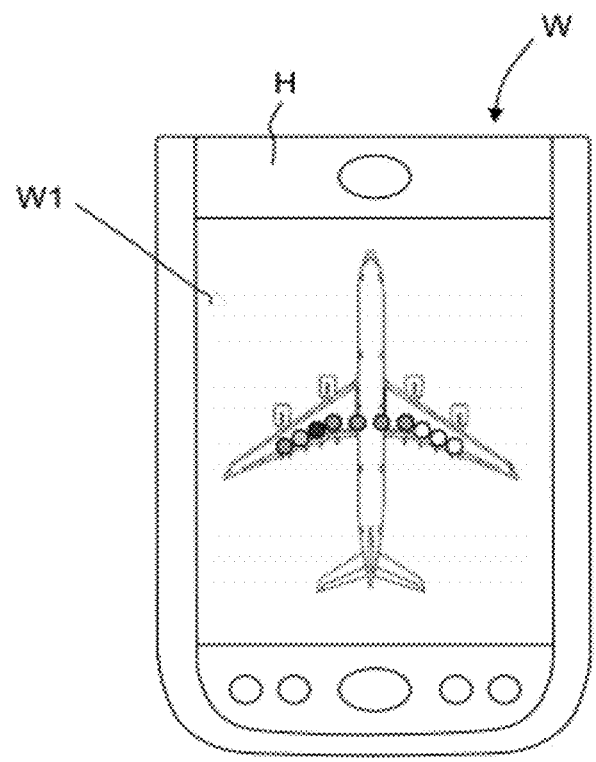
FIG. 8b shows, as compared with the display options represented in FIG. 8a, a further practical example of a diagnostic display for a maintenance device usable for the diagnostic system of the invention or the diagnosing method of the invention and realized as a hand-held apparatus, wherein the display contents represented by way of example are intended for use in the maintenance of an aircraft.

It is particularly advantageous if housing parts according to the invention and having movable parts that are bathed in a lubricant are monitored by a cordless diagnostic system as illustrated, by way of example, in FIGS. 8a and 8b.

FIGS. 8a and 8b each show a hand-held apparatus as a practical example of an external processing device for a cordless diagnostic system having integrated therein a processing unit for receiving and for processing sensor signals which are detected by the sensors 41 in a housing part 10 of the invention and emitted by the associated transceivers, as well as a display means. On the display means in FIG. 8b the example of an aircraft is used in order to visualize the utilization of several housing parts 10 of the invention which are installed in certain positions on the wings of the aircraft which are illustrated by respective circles.

The sensors situated in the closure devices 20 of housing parts of the invention that are employed on the aircraft emit sensor signals to transceivers 50 which are equally integrated in the closure devices 20 of the housing parts, which in turn transmit them to the external processing unit. The processing unit recognizes the housing part of origin of a sensor signal and displays this on the display means of the hand-held apparatus. In addition the processing unit evaluates the arriving sensor signals in order to draw conclusions concerning the condition of the lubricant in the respective housing parts and display diagnostic information as shown, e.g., in FIG. 6a.

The separate maintenance device W may in particular comprise a transceiver for receiving sensor signals from the transceiver 50 associated to the sensor device 40, wherein the maintenance device includes a processing function for determining, based on the sensor signal, a value for the operational condition of a lubricant present in the housing part. The separate maintenance device W may also, e.g. due to a corresponding input thereto, generate a control command which is transmitted via the transceiver 50 of the closure device 20 to the sensor device 40 and which activates the sensor device 40 to perform a measurement.

The maintenance device W may comprise a display device W1 for displaying the sensor quantities and/or determined maintenance information. A practical example of a display format that may be represented by means of the display device may include: an area W1a in which a definition or indication of at least one respective retrieved or displayed sensor and/or at least one component in which the respective sensor is installed are represented, and an area W1b in which the technical status of the respective displayed sensor is shown. As is furthermore shown schematically in FIG. 8a, the display format may be such that different sensors 41 or sensor devices 40 or components such as actuators, for instance, in which these are installed, are listed in a row form and, for example, laterally to the right from them three evaluation columns W11, W12, W13 having, e.g., the form of three display options that may be marked and are arranged side by side in the same row and, e.g., luminous indicators are provided, which is indicated only schematically in FIG. 8a. Marking or non-marking of fields within one respective row may thus be provided for one closure device each or for an apparatus having one or several closure devices, with the following meanings with regard to required maintenance measures:

marking of a field of the first column: no need to replace the lubricant, for the measured water content or the measured relative humidity in the lubricant container is below a first predetermined limit value;

marking of a field of the first column and additional marking of a field of the third column: no need to replace the lubricant, for although the measured water content or the measured relative humidity in the lubricant container is higher than the first predetermined limit value, it is nevertheless below a second predetermined limit value, but the necessity of replacing the lubricant must be monitored because replacing the lubricant may become necessary within a foreseeable period of time;

marking of a field of the second column: there is no sufficiently good signal quality in the transmission of signals or data between the maintenance device and the sensor devices 40 or components in question, and particularly the respective selected ones in which the respective selected sensor device 40 is installed;

marking of a field of the third column: replacement of the lubricant is required, for the measured water content or the measured relative humidity in the lubricant container is higher than the second predetermined limit value;

marking of none of the fields of the column in a row: no query was performed by means of the maintenance device W.

In the representation of FIG. 8a, some circular fields are tinted in grey. This is to give a schematic exemplary indication of the lubricant conditions detected at various sensor devices, depending on which fields of a respective row belonging to a sensor device are marked, i.e., tinted in grey in FIG. 8a.

In particular it may be provided that the first limit value is in the range between 6% and 10% and the second limit value is in the range between 12% and 16%.

The layout of fields may be realized in the display format such that one field each that can be marked is arranged in one respective column of a row. The respective field may have a circular shape, for example. The respective field associated to a row and a column may be realized as an area within a unified display area of, e.g., an LCD display area or as a lamp or separate luminous indicator.

In addition it may be provided that the fields of respective different columns are represented in different colors or assume different colors and/or are illuminated in different colors if they are to be marked or accentuated, for instance as the result of a query. For example it may be provided that the fields of the first column turn green, the fields of the second column turn yellow, and the fields of the third column turn red if they are to be marked or displayed.

For a corresponding realization of these checking functions in one of the practical examples according to the invention, the sensor device may include a function including a comparison function in which two limit values are stored or whereby two limit values are predetermined. The first limit value may be a value defined between 6% and 10% of relative humidity, and the second limit value may be a value defined between 12% and 16% of relative humidity. For example, the first limit value may be equal to 8%, and the second limit value may be equal to 12%. In this practical example the sensor device and/or the maintenance device W may be executed such that the detected measurement signal is supplied to the comparison function, with the comparison function determining in which one of the ranges delimited by the two limit values the respective detected signal value is situated (either below the first limit value or between the two limit values or above the second limit value), so that marking of the field in the corresponding column of the display format takes place on the basis of the identification of a range defined by the limit values. Hereby the urgency of a maintenance measure may be evaluated and displayed for the three ranges in accordance with one of the kinds presently described.

The method of the invention may generally be realized as a diagnosing method for monitoring a lubricant medium by means of a sensor device and a maintenance device associated thereto. In this case a measurement signal detected by a sensor device is supplied to comparison function, with the comparison function comparing the respective detected measurement signal to two limit values and identifying based on this comparison whether the respective detected signal value is situated in a first range below a first limit value or in a second range between the first and a second limit value greater than the first limit value, or in a third range above the second limit value. As a result of the identification of a range for the respective detected signal value, marking of one of three fields associated to a respective one of the ranges is effected in a display format of a display device.

In the diagnosing method it may be provided that the first limit value is a value for the relative humidity that is situated between 6% and 10%, and that the second limit value is a value for the relative humidity that is situated between 12% and 16%.

Alternatively or additionally it may be provided in the diagnosing method that in accordance with the display format of a display device for one respective sensor device whereby the measurement signal was detected, three fields each are associated to that sensor device, of which one field each is arranged in one of three columns of the display format, with the following meanings:

marking of a field of the first column means that the detected measurement signal is below the first predetermined limit value;

marking of a field of the first column and additional marking of a field of the third column means that the detected measurement signal is situated between the first predetermined limit value and the second predetermined limit value;

marking of a field of the second column means that there is no sufficiently good signal quality in the transmission of signals or data between the maintenance device and the respective, and particularly selected, sensor devices or the respective transceivers associated to them;

marking of a field of the third column means that the detected measurement signal is above the second predetermined limit value;

marking of none of the fields of the columns in a row means that no query was performed by means of the maintenance device W.

Marking of fields may be done with the aid of a multifunctional switch W2. Moreover the maintenance device W or the hand-held apparatus H may comprise a switch W3 for selecting all drivable sensors or sensor devices ("select all"). Moreover a switch W4 may be provided whereby selecting sensors or sensor devices may be precluded ("select none"). Moreover a switch W5 may be provided whereby in one or several ones of respective selected sensors or sensor devices of the maintenance device W an activation signal may be sent to these sensors or sensor devices, so that a measurement is carried out by these and/or a measurement value or signal value stored there is read out by them and sent to the sensors or sensor devices.

It may furthermore be provided that, for instance with the aid of a further switch W6, installation locations of sensors or sensor devices on the system or vehicle for which the maintenance device is being used are displayed. In FIG. 8b such a display is represented for a case in which the maintenance system and the sensor device of the invention is employed for an aircraft. In this embodiment, in which a satellite position determination sensor is integrated on one or several sensor devices and more specifically closure devices 20, an association of the respective sensor device may be effected by means of the determined position of the respective sensor device. This may be performed in addition or alternatively to the transmission of an address ID of the respective sensor device queried for a sensor value.

Accordingly, the maintenance device W may comprise a function module whereby a value for an operational condition of a lubricant present in the housing part may be determined from a sensor signal, and whereby the maintenance information required for a maintenance task may be transmitted to a display means and displayed with the aid of the display means.

Here it is particularly advantageous if the diagnostic system sensor transmits signals originating from different sensors that are mounted in one and the same housing part (e.g., in the inlet opening and in the outlet opening) to the processing unit and there compares them to each other, wherein a comparison function value is formed and underlaid the further processing as the result of the comparison. Thus it might be possible, e.g., to form a mean value of two sensor signals originating from one and the same housing part, or the smaller one of the two sensor signals would be discarded as a general rule. The latter option would, for instance, be a particularly simple and effective manner of proceeding for cases where one of the sensors in the inlet or outlet opening of the housing part is faulty and supplies a much too low sensor signal or no sensor signal at all.

Furthermore it is advantageous if the external processing unit compares the signals received from a sensor assembly group to predetermined limit values for these signals and visualizes on the display whether the received signal is situated within predetermined limit values for the signal (FIG. 8a).

For the case that a received sensor signal lies outside the range of the predetermined limit values, the processing unit may output a warning signal, in particular an acoustic or visual warning signal.

It is readily evident to the person having skill in the art that the principle of the diagnostic system illustrated in FIGS. 8a and 8b by way of example may be used with the maintenance device H and diagnosing method carried out thereby, also for assisting the maintenance of any kind of land, air, water or underwater vehicles. This is on the condition that a sensor means for generating and/or storing sensor signals is provided on at least one examination location for the diagnosis of faults on high-maintenance housing parts of vehicle, wherein the sensor signals are transmitted to a processing unit and the processing unit is operatively connected to a display means for displaying the sensor signals and/or the determined diagnostic information. In this case the sensors and transceivers are integrated into closure members for closing inlet/outlet openings for lubricant in a housing part having movable components in the body of the vehicle, and the transceiver in the closure member of the housing part transmits the sensor signals from the housing part to the processing unit.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A closure device for sealing an opening of a housing part from a lubricant, which comprises an internal space having arranged therein:
   at least one sensor device comprising a sensor for generating sensor signals corresponding to the operational condition of the lubricant, and
   at least one transceiver for receiving the sensor signals from the sensor device and for signal transmission of the sensor signals to an external reception unit,
   a power supply device for supplying electric power to the sensor device and to the transceiver,
   wherein the surface of one end portion is realized as a sensor surface for the detection of the sensor values; and
   wherein the sensor device comprises a planar capacitor which is constituted by two capacitor parts facing each other.

2. The closure device according to claim 1, wherein the closure device is realized as a screw configured to be inserted in a threaded reception of an inlet opening or outlet opening.

3. The closure device according to claim 1, wherein the closure device is realized as a bolt comprising a securing element configured to close the respective inlet opening or outlet opening by means of the bolt.

4. The closure device according to claim 1, wherein the transceiver is adapted to establish a wireless transmission connection that transmits the sensor signals to an external reception unit and is coupled to an antenna which is disposed on a surface of a second end portion situated opposite from the first end portion.

5. The closure device according to claim 1, wherein the sensor device comprises a humidity sensor configured to detect the water content of the lubricant and/or a temperature sensor configured to detect the temperature of the lubricant and/or a pressure sensor configured to detect the pressure of the lubricant.

6. The closure device according to claim 1, wherein the sensor device includes a measurement function wherein at least one temporal specification for the performance of a measurement and a function of performing the measurement are set up, which measurement function activates the sensor when the temporal specification is satisfied and detects sensor signals for the determination of sensor values.

7. The closure device according to claim 1, wherein the sensor device comprises a plate capacitor having two capacitor plates, and wherein the sensor surface of the first end portion that faces the interior of the housing part when the closure device is in the closing state and that is intended for entering into contact with the lubricant is partly configured as a groove, with two mutually facing surfaces of the side walls of the groove each forming an outer side of a respective one of the capacitor plates.

8. The closure device according to claim 7, wherein the groove is an annular groove.

9. A diagnostic system comprising a housing part of a lubricant container and a separate maintenance device,
   wherein the housing part comprises at least one opening and a closure device adapted to be inserted therein and being configured to seal an opening of the housing part from a lubricant, which comprises an internal space having arranged therein:
      at least one sensor device comprising a sensor configured to generate sensor signals corresponding to the operational condition of the lubricant, and
      at least one transceiver configured to receive the sensor signals from the sensor device and to transmit the sensor signals to an external reception unit,
      a power supply device configured to supply electric power to the sensor device and to the transceiver,
      wherein the surface of one end portion is realized as a sensor surface configured for the detection of the sensor values,
   wherein the at least one sensor device is adapted to generate sensor signals corresponding to the operational condition of the lubricant contained in the housing part and comprises a planar capacitor which is constituted by two capacitor parts facing each other,
   wherein the housing part and the closure device are configured such that in the state of the closure device in which it closes the housing part, a surface of a first end portion of the closure device faces the interior of the housing part so as to be in contact with the lubricant, wherein the surface is realized as a sensor surface configured for the detection of the sensor values,
   wherein the separate maintenance device comprises a transceiver configured to receive sensor signals from the transceiver associated to the sensor device, wherein the maintenance device includes a processing function module configured to determine, on the basis of the sensor signal, a value for the operational condition of a lubricant present in the housing part.

10. The diagnostic system according to claim 9, wherein the sensor device includes a measurement function wherein at least one timer for generating a temporal specification for the performance of a measurement and a function for performing the measurement is set up, wherein the timer is functionally communicated with the sensor such that the timer sends an activation signal to the sensor when the temporal specification is satisfied, wherein the sensor device is configured such that the sensor, in response to the activation signal, detects sensor signals for determining the operational condition of the lubricant, determines from these a sensor value corresponding to the operational condition of the lubricant, and stores it in a memory device of the sensor device, the maintenance device comprises an input device for retrieving a sensor value which, in response to an actuation of the input device, drives the transceiver associated to the sensor device and activates it to send the stored sensor signal to the maintenance device, and receives it.

11. The diagnostic system according to claim 10, wherein the sensor device is configured such that, in response to reception of a control command from the transceiver associated to the sensor device, it detects a sensor signal corresponding to an operational condition of the lubricant and sends it to the maintenance device.

12. The diagnostic system according to claim 9, wherein the sensor device comprises: a processing function configured to determine a value for the operational condition of a lubricant present in the housing part on the basis of the detected sensor signal, and a diagnosis function configured to communicate with the processing function for determining maintenance information from the respective determined value for the operational condition of a lubricant present in the housing part.

13. The diagnostic system according to claim 9, wherein the maintenance device includes a comparison function configured to communicate with the sensor device for supplying sensor signals, which is realized in such a way that the comparison function compares the respective detected measurement signal to at least one limit value and identifies, based on this comparison, whether the respective detected signal value is situated in a first range below this limit value or in a second range above this limit value, and wherein the maintenance device includes a display function which carries out, based on the identification of a range for the respective detected signal value, marking of at least one field or of one of two fields each allocated to one of the ranges, in a display format of a display device.

14. The diagnostic system according to claim 9, wherein the maintenance device includes a comparison function configured to communicate with the sensor device for supplying sensor signals, which is realized in such a way that the comparison function compares the respective detected measurement signal to two limit values and identifies, based on this comparison, whether the respective detected signal value is situated in a first range below a first limit value or in a second range between the first and a second limit value greater than the first limit value, or in a third range above the second limit value, and wherein the maintenance device includes a display function which carries out, based on the identification of a range for the respective detected signal value, marking of one of three fields each associated to one of the ranges, in a display format of a display device.

15. The diagnostic system according to claim 9, wherein the maintenance device comprises a function module whereby a value for an operational condition of a lubricant present in the housing part may be selected, whereby a maintenance information necessary for a maintenance task may be transmitted to a display and displayed on the display.

16. The diagnostic system according to claim 9, wherein at least two sensor devices are integrated in the housing part, wherein the maintenance device includes a comparison function configured to communicate with the transceiver of the maintenance device, and a comparison function value which is used as a value for the operational condition of a lubricant present in the housing part is formed on the basis of the sensor signals from two different sensor devices.

* * * * *